(12) United States Patent
Han et al.

(10) Patent No.: US 7,141,156 B2
(45) Date of Patent: Nov. 28, 2006

(54) ONE-POINT RECALIBRATION METHOD FOR REDUCING ERROR IN CONCENTRATION MEASUREMENTS FOR AN ELECTROLYTIC SOLUTION

(75) Inventors: Jianwen Han, Danbury, CT (US); Mackenzie E. King, Southbury, CT (US); Glenn Tom, New Milford, CT (US); Steven Lurcott, Sherman, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 387 days.

(21) Appl. No.: 10/833,192

(22) Filed: Apr. 27, 2004

(65) Prior Publication Data

US 2005/0236273 A1    Oct. 27, 2005

(51) Int. Cl.
    *G01N 27/26*    (2006.01)
(52) U.S. Cl. .......................... 205/775; 702/23; 702/65; 702/85; 73/1.03
(58) Field of Classification Search ..... 205/775–794.5; 702/23, 65, 85–107; 73/1.03, 61.42
    See application file for complete search history.

(56) References Cited

U.S. PATENT DOCUMENTS

| 6,709,561 | B1* | 3/2004 | Pavlov et al. .................. 205/81 |
| 2003/0188977 | A1* | 10/2003 | Chalyt et al. ................ 205/775 |
| 2003/0201191 | A1* | 10/2003 | Kovarsky et al. ........... 205/775 |

OTHER PUBLICATIONS

Alexander Milchev and Irene Montenegro, J. Electroanal. Chem., 333 (1992), pp. 93-102.

* cited by examiner

*Primary Examiner*—Nam Nguyen
*Assistant Examiner*—Anthony Fick
(74) *Attorney, Agent, or Firm*—Steven J. Hultquist; Intellectual Property Technology Law; Maggie Chappuis

(57) ABSTRACT

The present invention relates to a method for mathematically re-calibrating and adjusting an initial concentration analysis model that suffers from electrochemical measurement errors caused by surface state changes in the working/counter/reference electrode after extended usage. Specifically, such recalibration method reimburses long-term drift in the electrochemical measurements based on a single point testing.

23 Claims, 3 Drawing Sheets

ONE-POINT RECALIBRATION METHOD FOR REDUCING ERROR IN CONCENTRATION MEASUREMENTS FOR AN ELECTROLYTIC SOLUTION

BACKGROUND OF THE INVENTION

1. Field of the Invention

The present invention relates to a method for determining the concentrations of one or more components in an electrolytic solution, especially in a copper electrochemical deposition solution.

2. Description of the Related Art

In electrochemical deposition (ECD) process, the rigorous control of the relative proportions of respective inorganic and organic ingredients in the ECD bath is critical to the achievement of satisfactory results in the rate of metal film formation and the quality of the film so formed. During the use of the plating bath solution, the plating process may be affected by depletion of inorganic components and organic additives as well as by organic byproduct formation. The ECD bath chemistry therefore must be maintained by periodic replacement of a part or the entire ECD bath. It is therefore important to continuously or periodically monitor the concentrations of inorganic and/or organic components in the ECD bath, and responsively add respective components to the bath to maintain the composition of the bath in an effective state for the electrochemical deposition operation.

In electrochemical-based analysis of organic additive concentration in the ECD bath, the surface state of the working/counter/reference electrode changes with long term operation, due to contamination, corrosion, or re-crystallization of the electrode surface material, which causes drift in the measurement results. Corresponding recalibration or adjustment of the concentration analysis results therefore is required, which is time-consuming and complicated for onsite operation.

It is therefore an object of the present invention to provide a new method for one-point recalibration or adjustment of the concentration analysis results, to reimburse the drift in the measurement results based on one point testing and to provide a modified concentration analysis model with build-in drift reimbursement features.

Other objects and advantages will be more fully apparent from the ensuring disclosure and appended claims.

SUMMARY OF THE INVENTION

The present invention in one aspect relates to a method for reducing measurement error in concentration analysis of electrolytic solutions, comprising:

(a) establishing an initial model for determining concentration Y of a component of interest in electrolytic solutions based on a measurable parameter X that is correlative to Y, wherein correlation between X and Y in such initial model is expressed as $Y=f(X)$;

(b) providing a standard electrolytic solution that contains the component of interest at a known concentration $Y_s$;

(c) calculating a theoretical parameter value $X_s$ for the standard electrolytic solution, wherein $X_s=f^{-1}(Y_s)$;

(d) measuring the actual parameter value $X_o$ of such standard electrolytic solution;

(e) determining an adjustment factor e, wherein $e=X_s-X_o$;

(f) constructing a revised model that provides $Y=f(X+e)$ for future concentration determination of the component of interest; and (g) optionally, repeating steps (b)–(f) for model revision on a periodical or threshold basis.

In a preferred embodiment of the present invention, the electrolytic solutions are copper electrochemical deposition solutions that contain copper sulfate, chloride, sulfuric acid, and optionally one or more organic additives selected from the group consisting of suppressor, accelerator, and leveler.

However, applications of the present invention are not limited to analysis of copper electrochemical deposition solutions, and it can be broadly employed for analysis of electrochemical deposition solutions that contain other metal species, such as aluminum, silver, gold, iridium, palladium, tantalum, titanium, chromium, cobalt, tungsten, tin, lead, etc., and other electrochemical deposition solutions that are free of any metal components.

Another aspect of the present invention relates to a method for recalibrating a predetermined concentration analysis model, in which concentration Y of a target component in electrolytic solutions is determined by a measurable parameter X and a function $Y=f(X)$.

Such method comprising the steps of:

(a) providing a standard electrolytic solution that contains the target component at a known concentration $Y_s$;

(b) calculating a theoretical parameter value $X_s$ for such standard solution, based on $Y_s$ and inverse of the function $Y=f(X)$;

(c) measuring the actual parameter value $X_o$ of such standard solution;

(d) determining an adjustment factor e, wherein $e=X_s-X_o$; and (e) constructing a recalibrated concentration analysis model that provides $Y=f(X+e)$.

A still further aspect of the present invention relates to a method for reducing measurement error in concentration analysis of electrolytic solution, comprising:

(a) establishing an initial model for determining concentration Y of a component of interest in electrolytic solution based on a measurable parameter X that is correlative to Y, wherein correlation between X and Y in such initial model is expressed as $Y=f(X)$;

(b) providing a standard electrolytic solution that contains the component of interest at a known concentration $Y_s$;

(c) calculating a theoretical parameter value $X_s$ for the standard electrolytic solution, wherein $X_s=f^{-1}(Y_s)$;

(d) measuring the actual parameter value $X_o$ of the standard electrolytic solution;

(e) determining an adjustment factor e, wherein $$e = \frac{X_s}{X_0};$$

(f) constructing a revised model that provides $Y=f(X \times e)$ for future concentration determination of the component of interest; and (g) optionally, repeating steps (b)–(f) for model revision on a periodical or threshold basis.

A still further aspect of the present invention relates to a method for recalibrating a predetermined concentration analysis model, in which concentration Y of a target component in electrolytic solution is determined by a measurable parameter X and a function $Y=f(X)$, said method comprising the steps of:

(a) providing a standard electrolytic solution that contains the target component at a known concentration $Y_s$;

(b) calculating a theoretical parameter value $X_s$ for the standard solution, based on $Y_s$ and inverse of the function $Y=f(X)$;

(c) measuring the actual parameter value $X_o$ of the standard solution;

(d) determining an adjustment factor e, wherein $$e = \frac{X_s}{X_0};$$

(e) constructing a recalibrated concentration analysis model that provides $Y=f(X \times e)$.

Other aspects, features and embodiments of the present invention will be more fully apparent from the ensuing disclosure and appended claims.

DETAILED DESCRIPTION OF THE INVENTION, AND PREFERRED EMBODIMENTS THEREOF

In an electrochemical analytical cell used for analyzing sample copper ECD solutions, a cyclic electrical potential is applied between a first and a second electrode, both of which are immersed in the sample copper ECD solution for cyclic voltammetry (CV) scan thereof. During the CV scan, various components contained in the sample solution undergo reduction and oxidation in a cyclic manner, resulting in a characteristic current response curve that contains multiple reduction and oxidation current peaks, which are correlated with the component concentrations in such sample solution. For example, concentration of copper and/or sulfuric acid in such copper ECD solution can be determined by analyzing the copper and/or hydrogen reduction/oxidation peaks.

Further, the characteristic current response curve of a sample ECD solution can be compared with the current response curves of one or more calibration solutions that contain the component of interest at known concentrations, for estimation of the concentration of such component of interest in the sample solution.

Figure 1:
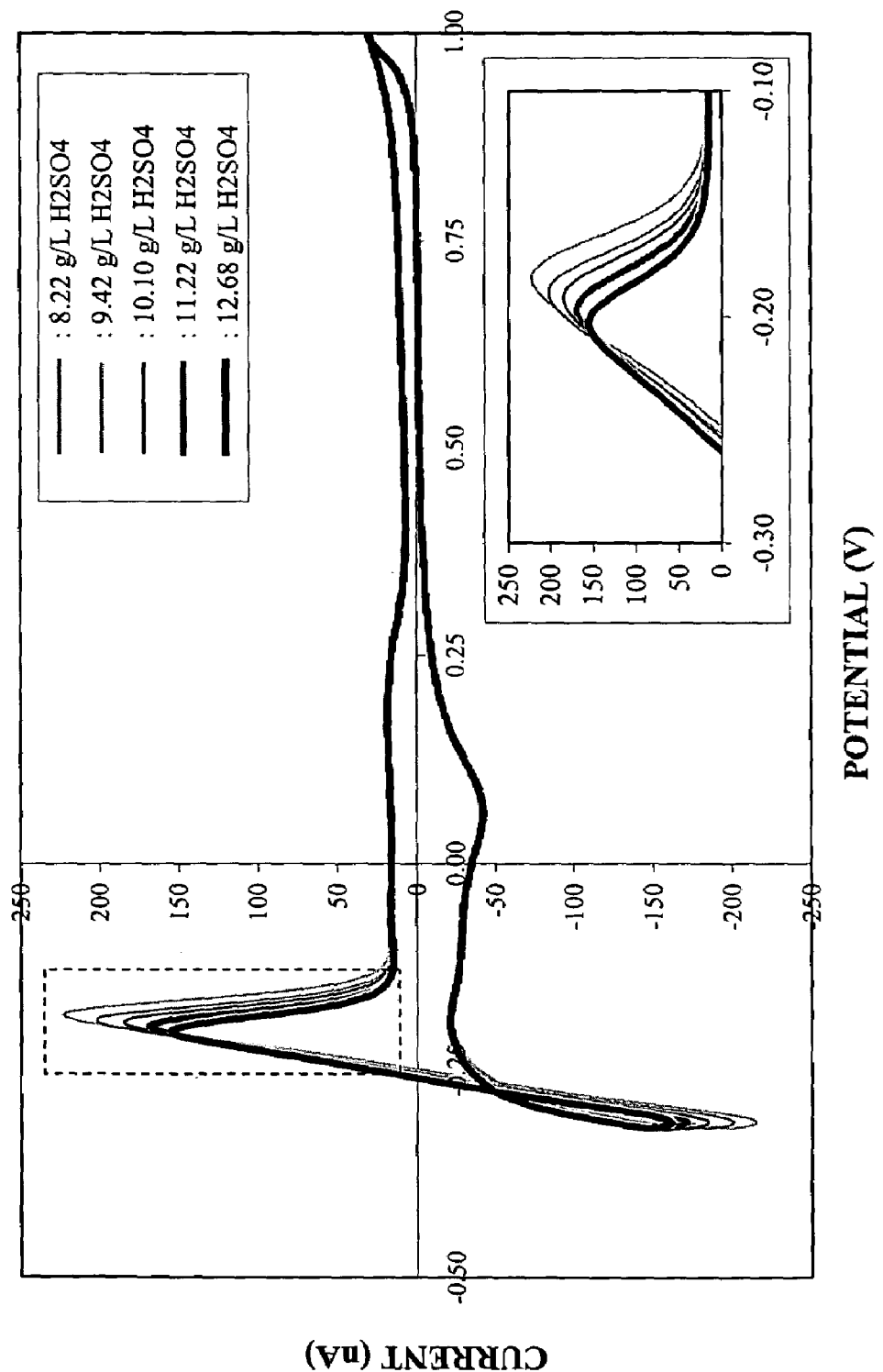
FIG. 1 shows five current response curves obtained under cyclic electric potentials for five electrolytic solutions, which contain copper ions at the same concentration and sulfuric acid at five different concentrations.

FIG. 1 shows the current response curves of five calibration solutions, as obtained under a cyclic electropotential that oscillates between −0.32 volt and +1.0 volt with a scan rate of about 300 mV/second. All the calibration solutions contain copper at the same concentration and the target component, i.e., sulfuric acid, at different concentrations. Specifically, the first calibration solution contains sulfuric acid at a concentration of about 8.22 g/L; the second calibration solution contains sulfuric acid at a concentration of about 9.42 g/L; the third calibration solution contains sulfuric acid at a concentration of about 10.10 g/L; the fourth calibration solution contains sulfuric acid at a concentration of about 11.22 g/L; the fifth calibration solution contains sulfuric acid at a concentration of about 12.68 g/L.

As shown in FIG. 1, the current response curves contain sharply distinguishable current peaks within the electrical potential range marked by the dotted rectangular box (approximately the copper oxidation potential range for Cu to become $Cu^+$), which can be selected for sulfuric acid concentration mapping.

Figure 2:
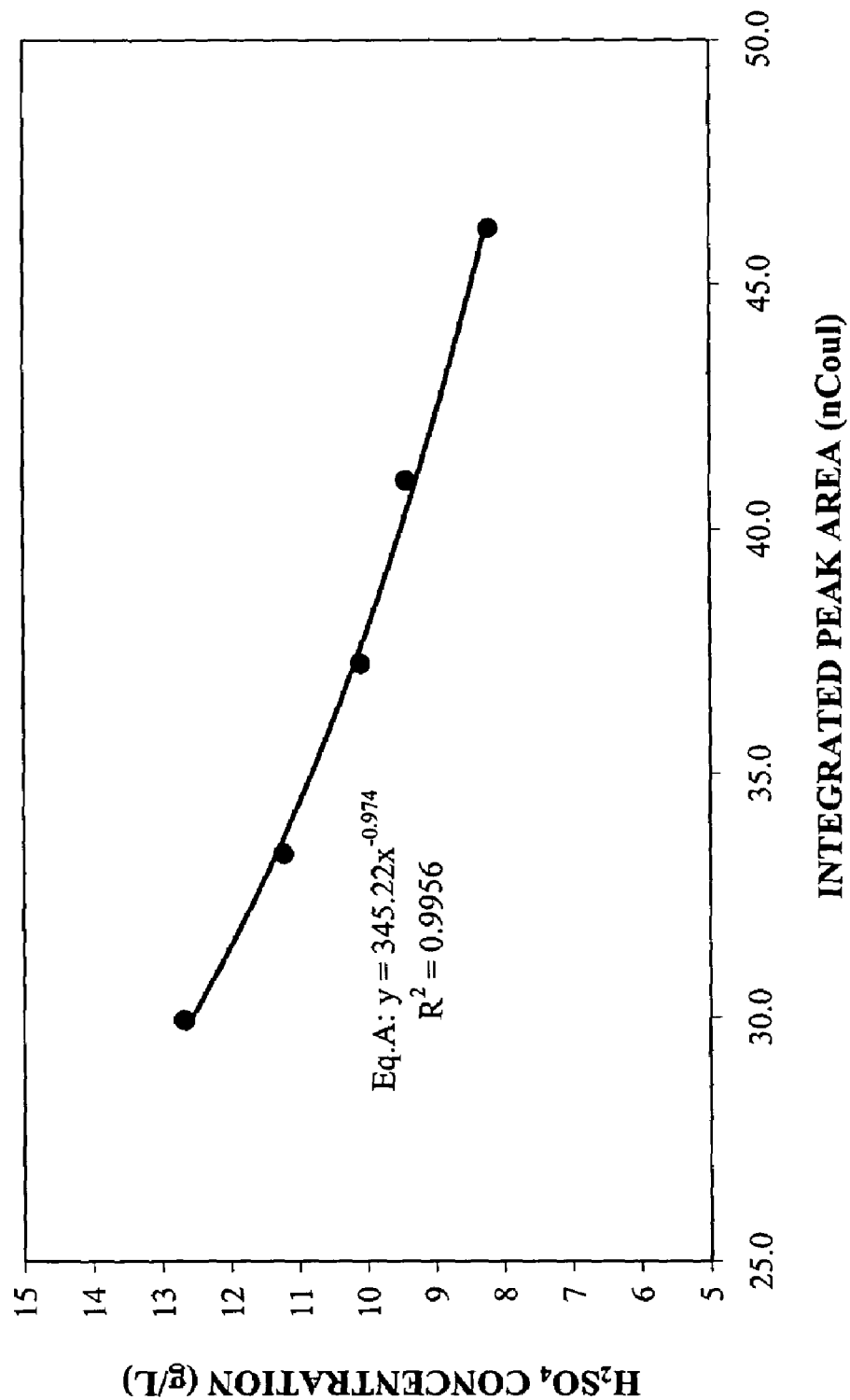
FIG. 2 shows an initial calibration curve that correlates sulfuric acid concentrations with the integrated areas of selected current peaks in the current response curves of FIG. 1.

Subsequently, the integrated areas of the selected copper oxidation peaks in the current response curves of FIG. 1 are calculated. The known sulfuric acid concentrations of the calibration solutions are then plotted as a function of such integrated peak areas, to form a calibration curve that quantitatively correlates the integrated current peak areas with the sulfuric acid concentrations, as shown in FIG. 2. An empirical equation A is preferably constructed on the basis of such calibration curve, which correlates the integrated current peak area X (in nCoul) with the sulfuric acid concentration Y (in g/L) via the following function:

$$Y=345.22 \cdot X^{-0.974}$$

Equation A and the initial calibration curve as shown in FIG. 2 can be used for mapping the concentration of sulfuric acid in sample copper ECD solutions that contain copper at the same concentration as the calibration solutions and sulfuric acid at unknown and potentially different concentrations.

However, after an extended period of time, the current responses measured from the sample copper ECD solutions will start to drift, due to changes in the surface state of the working/counter/reference electrode caused by contamination, corrosion, or re-crystallization of the electrode surface material. Consequently, the current response drift will result in significant errors in the sulfuric acid concentration determination.

Figure 3:
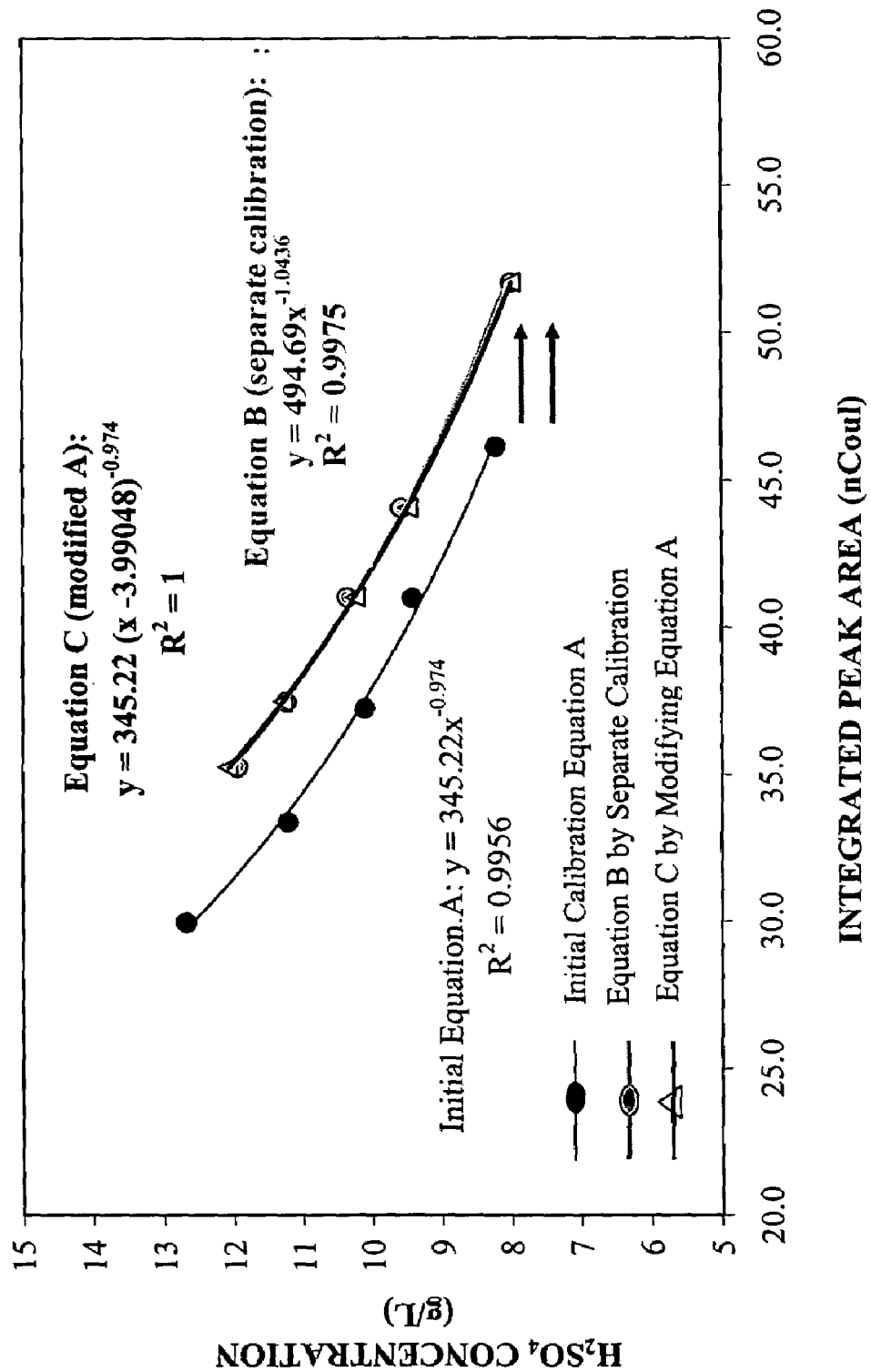
FIG. 3 compares the initial calibration curve of FIG. 2 with a first re-calibration curve that is obtained by re-correlating sulfuric acid concentrations with newly conducted measurements of the integrated peak areas, and a second re-calibration curve that is obtained by mathematically modifying the initial calibration equation.

One method for reducing such measurement caused by current response drift is to reconstruct a new calibration curve and a new empirical equation B (as shown in FIG. 3), based on the same method as described hereinabove and using the same group of calibration solutions that have been originally used for constructing the initial calibration curve and the initial empirical equation A. In other words, a new and independent round of calibration measurements is carried out to provide a new calibration curve and a new equation B containing the new function:

$$Y=494.69 \cdot X^{-1.0436}$$

which factors in the electrode surface state changes that have occurred during the initial measurement and the new measurement.

However, such complete reconstruction of the calibration curve and empirical equation is very time- and labor-consuming, and it significantly extended the down-time needed for system readjustment. Such extended down-time is particularly disadvantageous when the system requires periodic readjustments.

Therefore, the present invention provides a method for one-point re-calibration of the initial calibration curve and empirical equation, which requires only a single calibration test and provides a modified empirical equation that mathematically factors in the electrode surface state changes that have occurred since the initial measurement.

Specifically, a standard calibration solution that contains copper at the same concentration as the original calibration solutions and sulfuric acid (i.e., the target component) at about 9.90 g/L is provided. The known sulfuric acid concentration of 9.90 g/L is recorded as the standard sulfuric acid concentration $Y_s$. Based on the initial empirical equation A and $Y_s$, a standard integrated peak area, $X_s$, is calculated by inverting equation A, as follows:

$$X_s = -0.974\sqrt{\frac{Y_s}{345.22}}$$
$$= 38.4015$$

Subsequently, the actual integrated peak area, $X_o$, is calculated by CV scanning such standard calibration solution to obtain a characteristic current response curve (not shown) of such solution and calculating the integrated area of the copper oxidation current peak. The actual integrated peak area $X_o$ is about 42.392 nCoul.

Based on $X_s$ and $X_o$, an adjustment factor e is calculated as:

$$e = X_s - X_o = 38.4015 - 42.392 = -3.99048$$

Such adjustment factor e is employed to mathematically construct a modified equation C based on the initial equation A, while equation C provides:

$$Y = 345.22(X - 3.99048)^{-0.974}$$

A modified calibration curve (C) reflecting such modified equation C is shown in FIG. 3, in comparison with the initial calibration curve (A) and the new calibration curve (B) obtained by complete recalibration. It is evident that the modified calibration curve (C) closely maps the curve (B), indicating that the mathematically constructed equation C provides measurement results consistent with the empirically constructed equation B.

The one-point re-calibration method as described hereinabove can be generalized for modifying any initial concentration analysis model that correlates the concentration of a component of interest Y with a measurement parameter X, which can be the integrated peak area, as in the specific example described hereinabove, or any other variables that are correlative with the concentration of the component of interest and that can be measured from the sample electrolytic solution, including but not limited to, current peak height, plating/stripping potential, plating/stripping current, etc.

When the initial concentration analysis model describes the correlation between the concentration of the component of interest Y and the measurable parameter X as $Y=f(X)$, the one-point re-calibration method of the present invention provides a modified concentration analysis model that defines $Y=f(X-e)$ with an adjustment factor e.

Such adjustment factor e is obtained by providing a standard calibration solution that contains the component of interest at a known concentration $Y_s$, calculating a theoretical parameter value $X_s$ based on inverse of the function provided by the initial concentration analysis model, i.e., $X_s = f^{-1}(Y_s)$, measuring the actual parameter value $X_o$ for such standard calibration solution, and determining the difference between $X_s$ and $X_o$ (i.e., $e = X_s - X_o$).

Alternatively, the modified concentration analysis model may define $Y=f(X \times e)$ with an adjustment factor e that is determined by the ratio between $X_s$ and $X_o$ (i.e., $e = X_s/X_o$).

When cyclic voltammetry is employed for the concentration analysis, any anomaly in the shapes and/or magnitudes of various current peaks contained in the current response curves of the sample solutions constitutes a good indicator of electrode surface state changes. Therefore, the current response curves of the sample solutions can be continuously or periodically reviewed for determining the necessity of re-calibration or system adjustment. For example, the analysis protocol may be designed to responsively initiate a re-calibration cycle when changes in the height of certain current peaks reach a predetermined threshold. Alternatively, the analysis protocol may be designed to provide periodic re-calibration of the concentration analysis model, according to the method described hereinabove.

While the ensuing description is primarily directed to an electrochemical deposition (ECD) system for copper deposition, it will be recognized that the methodology of the invention are not thus limited, but rather generally extend to and encompass the determination of analytes in fluid media. For example, the invention is readily applicable to other ECD process applications, including deposition of aluminum, silver, gold, iridium, palladium, tantalum, titanium, chromium, cobalt, tungsten, etc., as well as deposition of alloys and deposition of amalgams such as solder.

Examples of additional applications of the invention other than ECD plating of semiconductor device structures include analysis of reagents in reaction media for production of therapeutic agents such as pharmaceutical products, and biotechnology applications involving the concentrations of specific analytes in human blood or plasma. It will therefore be appreciated that the invention is of broad application, and that the ECD system and method described hereafter is but one of a myriad of potential uses for which the invention may be employed.

While the invention has been described herein with reference to specific aspects, features and embodiments, it will be recognized that the invention is not thus limited, but rather extends to and encompasses other variations, modifications and alternative embodiments. Accordingly, the invention is intended to be broadly interpreted and construed to encompass all such other variations, modifications, and alternative embodiments, as being within the scope and spirit of the invention as hereinafter claimed.

What is claimed is:

1. A method for reducing measurement error in concentration analysis of electrolytic solution, comprising:
    (a) establishing an initial model for determining concentration Y of a component of interest in electrolytic solution based on a measurable parameter X that is correlative to Y, wherein correlation between X and Y in said initial model is expressed as $Y=f(X)$;
    (b) providing a standard electrolytic solution that contains said component of interest at a known concentration $Y_s$;
    (c) calculating a theoretical parameter value $X_s$ for said standard electrolytic solution, wherein $X_s = f^{-1}(Y_s)$;
    (d) measuring the actual parameter value $X_o$ of said standard electrolytic solution;
    (e) determining an adjustment factor e, wherein $e = X_s - X_o$;
    (f) constructing a revised model that provides $Y=f(X+e)$ for future concentration determination of the component of interest; and
    (g) optionally, repeating steps (b)–(f) for model revision on a periodical or threshold basis.

2. The method of claim 1, wherein said electrolytic solution comprises electrochemical deposition solution containing one or more metal components.

3. The method of claim 2, wherein said metal components are selected from the group consisting of aluminum, silver, gold, iridium, palladium, tantalum, titanium, chromium, cobalt, tungsten, tin, and lead.

4. The method of claim 1, wherein said electrolytic solution is free of metal components.

5. The method of claim 1, wherein said electrolytic solution comprises copper electrochemical deposition solution containing copper sulfate, chloride, and sulfuric acid.

6. The method of claim 5, wherein said copper electrochemical deposition solution further comprises one or more organic additives selected from the group consisting of suppressors, accelerators, and levelers.

7. The method of claim 5, wherein the component of interest is sulfuric acid.

8. The method of claim 5, wherein the component of interest is copper.

9. The method of claim 1, wherein the measurable parameter X is obtained by immersing first and second electrodes in the electrolytic solution, applying a cyclic electrical potential between said first and second electrodes, and analyzing current response of the electrolytic solution.

10. The method of claim 9, wherein the current response of the electrolytic solution contains one or more current peaks, and wherein said measurable parameter X is the integrated area of one of said current peaks.

11. The method of claim 1, wherein the initial model for determining concentration Y of the component of interest in electrolytic solution is established by:
   (i) providing multiple calibration electrolytic solutions containing the component of interest at unique, known concentrations;
   (ii) measuring the respective parameter X for each of said calibration electrolytic solutions; and
   (iii) constructing the initial model, by correlating said unique, known concentrations Y of the component of interest in the calibration solutions with the respective parameters X measured for said calibration solutions to form an empirical correlation function in which $Y=f(X)$.

12. A method for recalibrating a predetermined concentration analysis model, in which concentration Y of a target component in electrolytic solution is determined by a measurable parameter X and a function $Y=f(X)$, said method comprising the steps of:
   (a) providing a standard electrolytic solution that contains said target component at a known concentration $Y_s$;
   (b) calculating a theoretical parameter value $X_s$ for said standard solution, based on $Y_s$ and inverse of the function $Y=f(X)$;
   (c) measuring the actual parameter value $X_o$ of said standard solution;
   (d) determining an adjustment factor e, wherein $e=X_s-X_o$;
   (e) constructing a recalibrated concentration analysis model that provides $Y=f(X+e)$.

13. The method of claim 12, wherein said electrolytic solution comprises electrochemical deposition solution containing one or more metal components.

14. The method of claim 13, wherein said metal components are selected from the group consisting of aluminum, silver, gold, iridium, palladium, tantalum, titanium, chromium, cobalt, tungsten, tin, and lead.

15. The method of claim 12, wherein said electrolytic solution is free of metal components.

16. The method of claim 12, wherein said electrolytic solution comprises copper electrochemical deposition solution containing copper sulfate, chloride, and sulfuric acid.

17. The method of claim 16, wherein said copper electrochemical deposition solution further comprises one or more organic additives selected from the group consisting of suppressors, accelerators, and levelers.

18. The method of claim 16, wherein the component of interest is sulfuric acid.

19. The method of claim 16, wherein the component of interest is copper.

20. The method of claim 12, wherein the measurable parameter X is obtained by immersing first and second electrodes in the electrolytic solution, applying a cyclic electrical potential between said first and second electrodes, and analyzing current response of the electrolytic solution.

21. The method of claim 20, wherein the current responses of the electrolytic solution contain one or more current peaks, and wherein said measurable parameter X is the integrated area of one of said current peaks.

22. A method for reducing measurement error in concentration analysis of electrolytic solution, comprising:
   (a) establishing an initial model for determining concentration Y of a component of interest in electrolytic solution based on a measurable parameter X that is correlative to Y, wherein correlation between X and Y in said initial model is expressed as $Y=f(X)$;
   (b) providing a standard electrolytic solution that contains said component of interest at a known concentration $Y_s$;
   (c) calculating a theoretical parameter value $X_s$ for said standard electrolytic solution, wherein $X_s=f^{-1}(Y_s)$;
   (d) measuring the actual parameter value $X_o$ of said standard electrolytic solution;
   (e) determining an adjustment factor e, wherein
   $$e = \frac{X_s}{X_0};$$
   (f) constructing a revised model that provides $Y=f(X\times e)$ for future concentration determination of the component of interest; and
   (g) optionally, repeating steps (b)–(f) for model revision on a periodical or threshold basis.

23. A method for recalibrating a predetermined concentration analysis model, in which concentration Y of a target component in electrolytic solution is determined by a measurable parameter X and a function $Y=f(X)$, said method comprising the steps of:
   (a) providing a standard electrolytic solution that contains said target component at a known concentration $Y_s$;
   (b) calculating a theoretical parameter value $X_s$ for said standard solution, based on $Y_s$ and inverse of the function $Y=f(X)$;
   (c) measuring the actual parameter value $X_o$ of said standard solution;
   (d) determining an adjustment factor e, wherein
   $$e = \frac{X_s}{X_0};$$
   (e) constructing a recalibrated concentration analysis model that provides $Y=f(X\times e)$.

* * * * *